(12) United States Patent
Hall et al.

(10) Patent No.: US 6,997,446 B2
(45) Date of Patent: Feb. 14, 2006

(54) SPRING MEMBER FOR ROTATIONAL ACTION

(75) Inventors: Scott E. Hall, Issaquah, WA (US); Bruce E. Taber, Bothell, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/028,200

(22) Filed: Dec. 20, 2001

(65) Prior Publication Data

US 2003/0205858 A1 Nov. 6, 2003

(51) Int. Cl.
*F16F 1/14* (2006.01)
*A46B 9/04* (2006.01)
*A61C 3/00* (2006.01)

(52) U.S. Cl. .............. 267/154; 267/150; 15/167.1; 433/118

(58) Field of Classification Search ............. 267/154, 267/150, 182, 161, 160, 164, 162; 15/22.1, 15/22.2, 167.1, 167.2, 23, 28; 433/118, 131, 433/216; 403/120, 166, 225, 220
See application file for complete search history.

(56) References Cited

U.S. PATENT DOCUMENTS

| | | | | | |
|---|---|---|---|---|---|
| 1,749,393 | A | * | 3/1930 | Pflimlin ..................... 492/57 |
| 2,238,380 | A | * | 4/1941 | Almen ...................... 267/283 |
| 2,819,892 | A | * | 1/1958 | Huff ......................... 267/154 |
| 2,836,912 | A | * | 6/1958 | Ranucci ..................... 40/470 |
| 2,915,306 | A | * | 12/1959 | Hickman ................... 267/281 |
| 3,019,622 | A | * | 2/1962 | Fermier ....................... 464/86 |
| 3,081,991 | A | * | 3/1963 | Swainson ................... 267/154 |
| 3,124,342 | A | * | 3/1964 | Ormond .................... 267/154 |
| 3,272,492 | A | * | 9/1966 | Jones ........................ 267/154 |
| 3,276,762 | A | * | 10/1966 | Thomas ..................... 267/154 |
| 3,545,286 | A | * | 12/1970 | Stenstrom .................. 248/604 |
| 5,381,576 | A | * | 1/1995 | Hwang ....................... 15/22.1 |
| 5,417,407 | A | * | 5/1995 | Gordon ..................... 267/154 |
| 5,611,524 | A | * | 3/1997 | Gordon ..................... 267/154 |
| 5,690,322 | A | * | 11/1997 | Hay .......................... 267/148 |
| 6,068,821 | A | * | 5/2000 | VanDeGraaf .............. 422/300 |
| 6,398,444 | B1 | * | 6/2002 | Salmela ....................... 403/53 |
| 6,422,791 | B1 | * | 7/2002 | Pallini et al. ............ 405/224.2 |
| 6,746,182 | B1 | * | 6/2004 | Stonesifer et al. ....... 405/224.2 |
| 2003/0204924 | A1 | * | 11/2003 | Grez et al. .................. 15/22.1 |

FOREIGN PATENT DOCUMENTS

FR 2028553 A 9/1970
SU SU 911076 * 3/1982 ............... 267/154

* cited by examiner

Primary Examiner—Thomas Williams

(57) ABSTRACT

The rotational spring includes a base member which is in the form of a ring and includes elements for fixedly attaching it to a body of an appliance, such as a power toothbrush, which includes a drive element such as a drive shaft portion of a motor. Also included is an upper member in the form of a disc having a central opening through which the drive shaft is fitted, such that the disc member rotates with rotation of the drive shaft. Three leg members extend between the upper disc member and the base ring member. The spring is made from a material and is so configured and arranged that it has a symmetric spring rate for clockwise and counter-clockwise rotation.

24 Claims, 4 Drawing Sheets

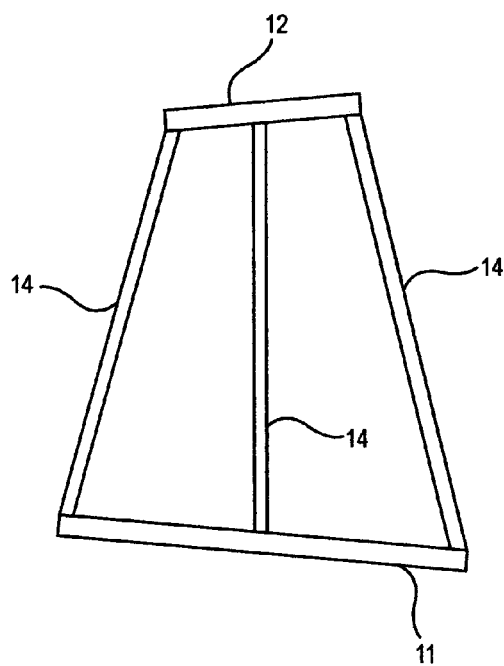
FIG.4
FIG.5
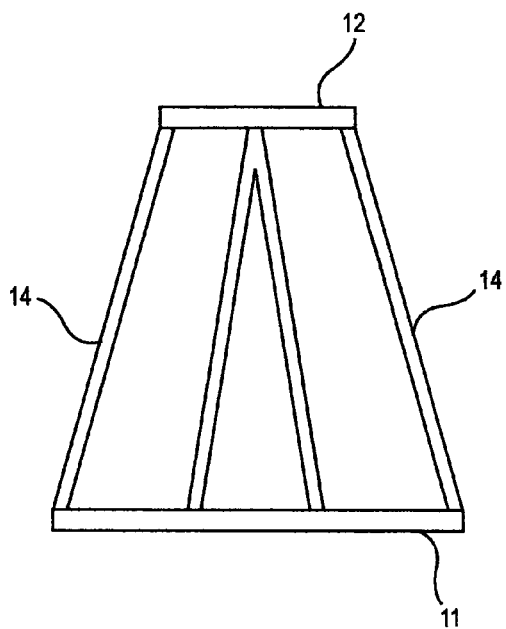
FIG.6A
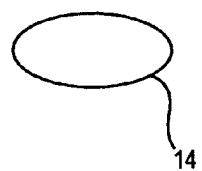
FIG.6B
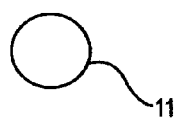
FIG.7
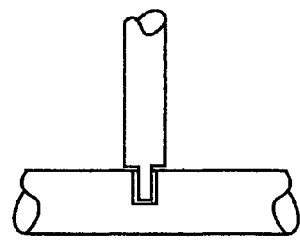

SPRING MEMBER FOR ROTATIONAL ACTION

TECHNICAL FIELD

This invention relates generally to springs, and more specifically concerns springs which are designed for rotational action.

BACKGROUND OF THE INVENTION

A rotational spring refers to a spring which twists in one direction under force, storing energy, and then, when the force is released, returns to or toward its original position. Such rotational springs are in general well known, and numerous arrangements accomplish the basic rotational action. It is typically desirable, although not necessary, in certain applications that a rotational spring have a symmetrical spring rate (in both the clockwise and counter-clockwise directions), while at the same time being inexpensive and convenient to manufacture. The present invention is a low-cost rotational spring with a symmetrical spring rate.

DISCLOSURE OF THE INVENTION

Accordingly, the present invention is a spring adapted for rotational action, comprising: a first member adapted for attachment by an appliance body member; a second member spaced apart from the first member and adapted to receive a driving member, wherein when the driving member moves through a selected range of movement, the second element rotates in response thereto; and at least two leg members connecting the first and second members, wherein when the driving member moves to an end point of its range of movement, having rotated the second member with the leg members attached thereto, the energy stored in the spring thereby tends to return the spring toward its original position.

In a somewhat different arrangement of the spring, there is no first element but the leg members have portions at the free ends thereof which are adapted for secure attachment of the spring to the appliance body, to provide the desired rotational action.

BRIEF DESCRIPTION OF THE DRAWINGS

FIG. 4 is a diagram showing another alternate arrangement of the rotational spring.

FIG. 5 is a diagram showing another alternate arrangement of the rotational spring.

FIGS. 6A and 6B are cross-sectional diagrams showing alternative cross-sections of the leg members of the rotational spring.

FIG. 7 is a diagram showing the connection of the leg members in the rotational spring.

BEST MODE FOR CARRYING OUT THE INVENTION

Figure 1:
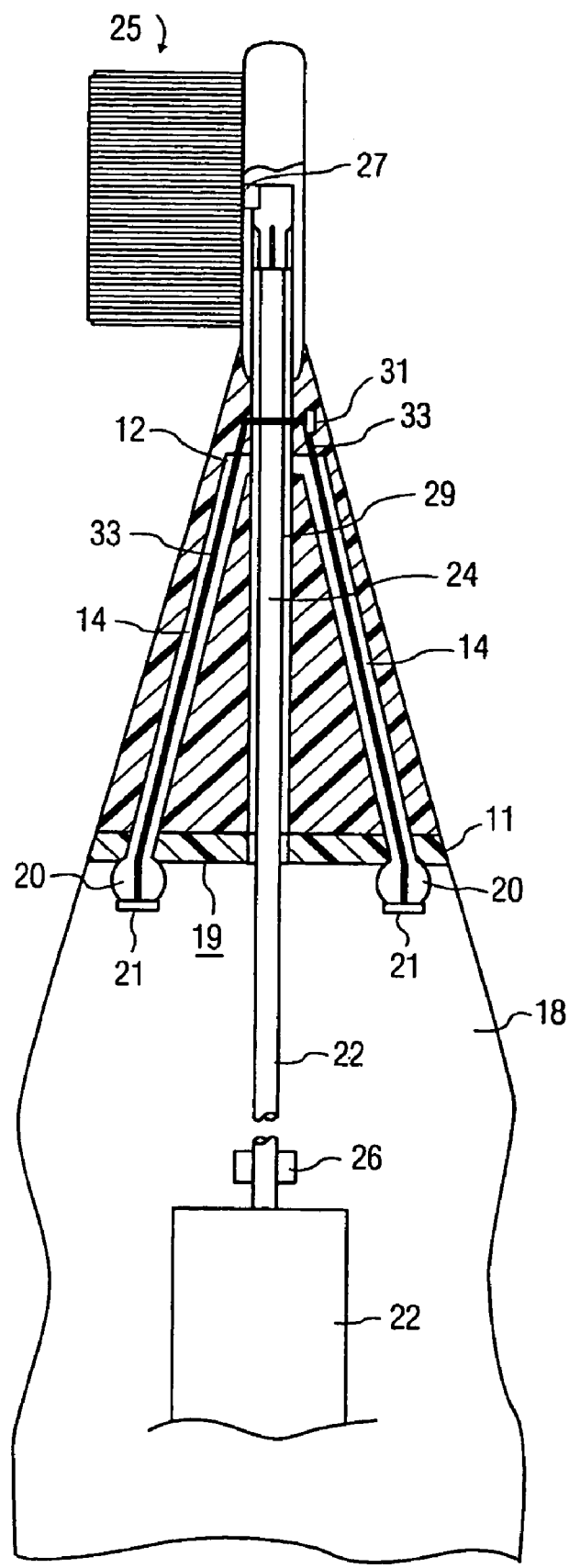
FIG. 1 is a side elevational view showing the rotational spring of the present invention in the context of a rotary drive power toothbrush.
Figure 2:
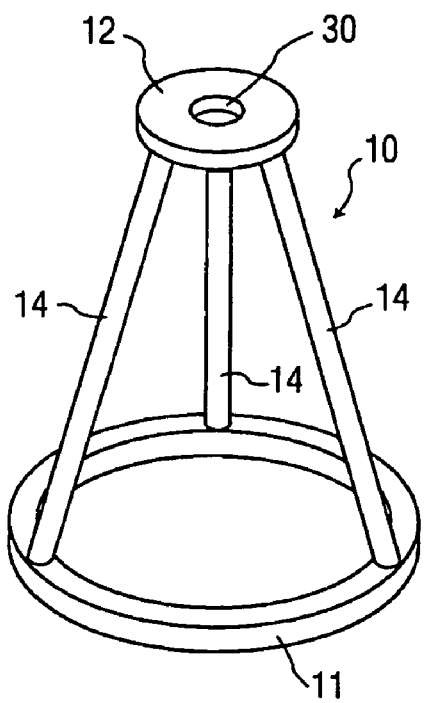
FIG. 2 is a simplified diagram showing the rotational spring of the present invention in a three-legged configuration.

FIGS. 1 and 2 show the rotational spring of the present invention, with FIG. 1 being shown in the context of a particular application, i.e. a rotary drive power toothbrush. It should be understood, however, that the rotational spring of the present invention is not limited to use with a power toothbrush. Any similar appliance, wherein a tool or head member rotates back and forth through a limited arc, is a possible candidate for the rotational spring shown and described herein.

The rotational spring of the present invention, shown generally at 10, in the embodiment of FIGS. 1 and 2, includes a ring-like base member 11, a circular plate or disc upper member 12 and a plurality of leg members 14 which extend between base member 11 and the plate member 12. In the present invention, rotational spring 10 includes at least two leg members 14, although three substantially equally spaced leg members are presently preferred. It should be understood, however, that more than three leg members can be used.

The base member 11 has a diameter which can vary, depending upon the article to which it is fixed. The cross-sectional configuration of the base member can also vary. It can be circular, square, rectangular, elliptical or some other configuration. The base member 11 will remain fixed in position during the rotational action of the spring. Referring to FIG. 1, the base member 11 is shown in the configuration of a ring, abutting the upper surface 19 of a handle portion 18 of a power toothbrush.

Extending downwardly from base member 11 in FIG. 1 (not shown in FIG. 2) are a plurality of connecting members 20, which fit securely into the body of handle 18. The connecting members can be snap-fitted to the handle, or secured by some other similar means, which securely position the base member into handle 18 (or the top portion of another appliance). The number of connecting members 20 and their arrangement can vary. While the connecting members are shown as extension of the leg members, that is not necessary. They can extend from any part of base member 11. Further, other attaching means can be used to secure the base member to the handle. It is important, however, that the connections between base member 11 and the handle 18 be secure, because, as indicated above, when the spring is rotated, base member 11 must remain fixed in position, although in some cases, the arrangement is such that there is some "lost motion", i.e. member 11 will initially rotate a small amount before becoming fixed.

Also, in another particular embodiment, member 11 could be just a seal between a head portion of a toothbrush (or other appliance) and the body of the appliance. The connecting members 20 at the end of the legs provide the secure attachment to the body of the appliance. In such a case, the spring comprises the driven member (member 12 in FIGS. 1 and 2) and at least two legs which extend therefrom with connecting members at the ends thereof for secure connection to the body of the appliance.

FIG. 1 shows the body of toothbrush handle 18, which will typically include a motor 22 and a drive shaft 24, which is supported by a circular bearing 26. Drive shaft 24 will rotate in operation through a predetermined arc. Drive shaft 24 extends upwardly through the center of ring-shaped base member 11. The arrangement of FIG. 1 as part of a power toothbrush, however, is for illustration only, to clarify the operation of the rotational spring of the present invention, and should not limit the scope of the present invention.

Upper member 12 is a relatively thin disc-like element, with a central opening 30 (shown clearly in FIG. 2) which accommodates the drive shaft 24 of the appliance device with which the spring is used, such as a toothbrush in FIG. 1. Opening 30 is designed to mate with the cross-sectional configuration of the drive shaft 24 and is typically fitted to the drive shaft by a press-fit, so that rotation of the drive shaft will rotate upper member 12. The cross-sectional configuration of the drive shaft and the configuration of the opening in member 12 can be square, hexagonal or other configuration which may assist in mutual rotation. Upper member 12 adds inertia to the rotational spring and is responsible for part of the overall flexure of the spring and as such absorbs energy during rotation of the spring produced by action of the driving element, e.g. drive shaft 24.

The leg members 14, as indicated above, extend directly between and connect base member 11 and upper member 12. While the diameter of the upper member 12 is typically selected to be as close as possible to the diameter of the lower base member 11 (and in some cases could be the same diameter), typically the upper member is somewhat smaller in diameter, so that leg members 14 angle inwardly between the lower base member 11 and upper plate member 12, as shown in FIGS. 1 and 2. The cross-sectional configuration of the leg members can vary, like the cross-sectional configuration of the base member 11, e.g. circular, square, rectangular or elliptical. Each shape has a somewhat different functional characteristic. It has been discovered that generally elliptical tends to be optimal relative to the combined torsional and bending loading of the rotational spring. A circular configuration tends to reduce stress in torsional loading, while rectangular tends to reduce stress in bending-type loading.

As indicated above, different numbers of legs can be used, although there must be at least two. The legs can bifurcate between the upper member and the base member. The length of the legs (determined by the distance between members 11 and 12 and their relative diameters) will assist in determining the spring rate of the rotational spring 10. The spring rate will decrease with the length of the spring. While leg members 14 typically will be straight, they can also be bent or curved to some extent. They can remain constant in size or cross-section, or they can vary to some extent along their length, which can be used to manipulate the tension along the length of the legs.

Leg members 14 will typically be fixedly connected to both the base member 11 and the upper member 12, although different kinds of connections can be made to produce different effects. For instance, a pin joint (at either end) can be used, with the axis of the pin being coplanar with the axis of the motion of the spring. This results in a free-bending motion of the spring. Free torsion motion can be achieved with a bearing-type of mount for the leg members; such a mount can also be used at either end of the leg members. Still further, a key-hole (slot) arrangement can be used that allows some freedom in the overall range of motion of the spring, i.e. the end of the leg is free to move a very short distance following initial action of the drive shaft before the twisting action on the legs begins. When there is no slot, twisting begins upon initial action of the drive shaft.

Base member and upper member and the leg members can be made of various materials. For instance, they can be made from metal or plastic, for instance, injection-molded elastomeric material. Any material, however, must have the capability of repeatedly returning to or toward its original position after it has been twisted or rotated in one direction. It must provide consistent, long-lived action.

The members 11 and 12 can be parallel, so that the free end member (member 12 in FIG. 1) exhibits rotational motion. They also can be non-parallel, in which case the free end member will exhibit both rotational and translational motion. In another variation, the spring could be generally tubular between the two members or conical, such as shown in FIGS. 1 and 2. This will affect both the spring rate and the loading on the leg members during rotation of the spring.

Figure 3:
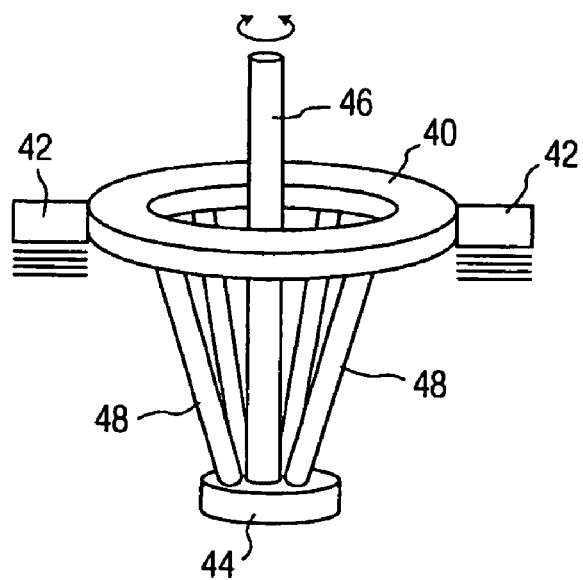
FIG. 3 is a simplified diagram showing an alternative arrangement of the rotational spring of the present invention.
Figure 8:
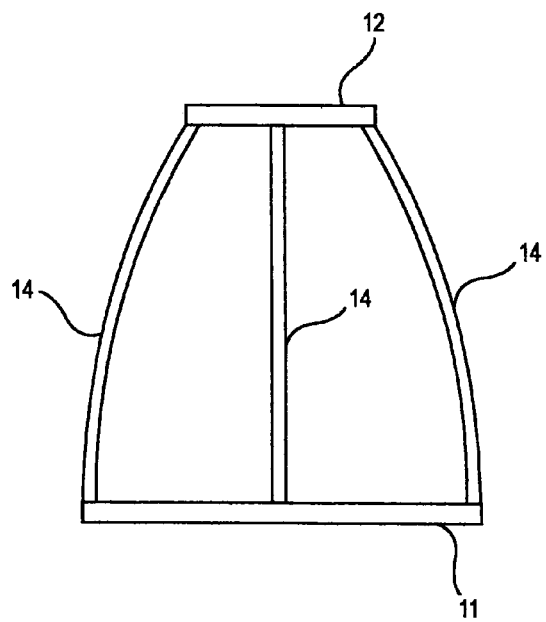
FIG. 8 is a diagram showing another alternate arrangement of the rotational spring.
Figure 9:
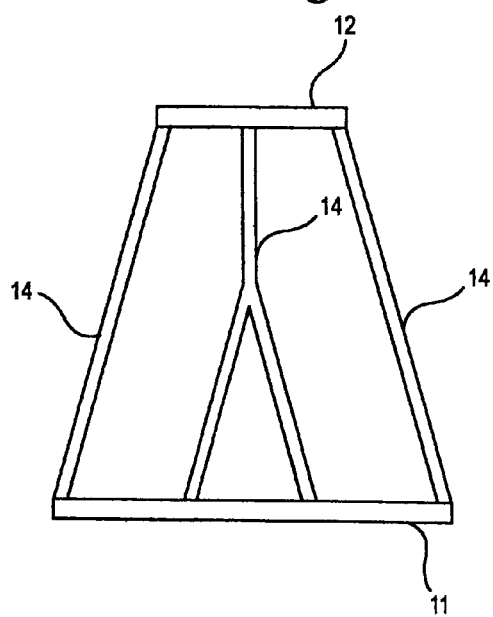
FIG. 9 is a diagram showing another alternate arrangement of the rotational spring.
Figure 10:
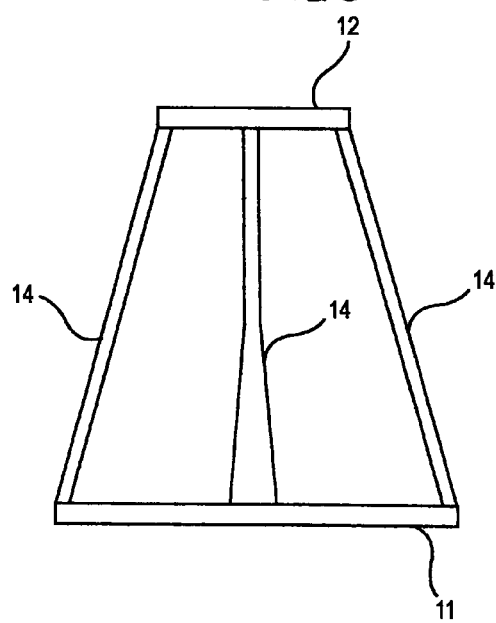
FIG. 10 is a diagram showing another alternate arrangement of the rotational spring.

In FIGS. 1 and 2, the base member 11 is fixed by attachment to handle 18 and the upper member 12 is driven by drive shaft 24 and rotates in operation, twisting the leg members 14. However, the base member could be the rotating, driven member and the upper member could be the fixed member. This is illustrated in FIG. 3. The upper member 40 is ring-like and is fixedly supported by element 42, which surrounds or partially surrounds element 40. The base member 44 is free to rotate and is driven by the oscillating drive shaft 46. The base and upper members are connected by leg members 48. FIG. 3 thus illustrates that the upper and lower members, respectively, can be either fixed or driven.

In a toothbrush embodiment, rotational spring 10 of the present invention is part of a removable head portion of the toothbrush. This arrangement can be used to advantage relative to a number of possible special structural features of the toothbrush. For instance, referring to FIG. 1, elasto-resistive (or piezoelectric) pads 21 could be used at the base of the connecting members 20 in the handle to sense a reactive load on the spring assembly, or electrical connections could be placed in the connecting members to permit communication with elements, such as a microchip, in the head portion. Pressure information can be routed from the pads 21 to a microprocessor (not shown) or similar device in handle 18 to provide an indication of the load on the spring 10. Further, there is room in the head portion for a fluid path line 29 from a reservoir (not shown) in the handle through the interior of the spring (adjacent the drive shaft) and then into a brush portion 25. A check valve 27 could be positioned in the brush portion 25 for control of the exit of fluid. A microchip 31 also could be imbedded into the spring structure (or a surrounding element) which would provide information concerning the identification of the head portion. Wire connecting elements 33 could extend from the chip 31 through the leg members 14 down to the electrical connections in connecting members 20.

In operation of the spring arrangement of FIG. 1, motor 22 will rotate drive shaft 24 in one rotational direction through a certain selected arc toward its original position. The spring 10 will then rotate via the releasing of the stored force, back through that same arc. In certain arrangements, the spring will return fully to its original position. The base member, as indicated above, will remain fixed in position during this action, with some lost motion in certain arrangements. The upper member will move slightly up and down as drive shaft 24 and the elements of rotational spring 10 (except base member 11) twist. The amount of twist will depend upon the amount of rotational force applied. However, the upper member 12 will desirably remain substantially in parallel with the plane of the base member, i.e. it will not tilt or bend off the Z (vertical) axis. Typically, the upper member will rotate in the range of $\pm 7°$–$\pm 10°$ about a central node point, thereby providing an overall arc of 14–20°. As indicated above, while the spring twists about its Z axis, it does not produce movement into the X-Y plane and does not bend about the X-Y axis. An odd number of legs will orient the brush portion 25 (or other tool) in one direction. With an even number of legs, multiple orientations are possible.

The rotational spring of the present invention surrounds the drive member for the spring. In one embodiment, the spring is unitary. It could also be segmented. The spring rate can be varied by selecting the materials of the spring and the dimensions of the spring as well as the number of legs. An elastomeric or other overmold can be used over the leg members to provide an enclosure for the spring forming a complete head portion for the appliance.

The rotational spring of the present invention, surrounding the drive member, eliminates multiple springs or springs which must move around a drive shaft in typical rotational spring arrangement. The present spring, while accomplishing a symmetric spring rate and providing reliable, consistent operation, is relatively inexpensive and easy to manufacture.

Although a preferred embodiment of the invention has been disclosed here for purposes of illustration, it should be understood that various changes, modifications and substitutions may be incorporated without departing from the spirit of the invention, which is defined by the claims which follow.

What is claimed is:

1. A spring adapted for rotational action, comprising:
   a first member substantially fixably attached to an appliance body member, the first member having an open center area extending through said first member to permit an appliance driving member which rotates in operation to extend freely therethrough, wherein the first member is a lower ring member which substantially encircles the driving member;
   a second member spaced apart from the first member and adapted to receive said appliance driving member, wherein when the driving member moves through a selected range of rotational movement, the second member rotates in response thereto, wherein the second member is an upper disc having a central opening through which the driving member is tightly fitted in such a manner that as the driving member rotates, the second member rotates therewith relative to the first member; and
   at least two leg members connecting the first and second members, wherein the leg members are constructed and arranged and characterized such that when the driving member moves to end points of its range of rotational movement, having rotated the second member with the leg members attached thereto, the energy stored in the spring thereby tends to return the spring toward its original center position.

2. An article of claim 1, wherein the spring forms part of a head portion of a power toothbrush and wherein the spring includes connecting members which connect the spring to a handle portion of the toothbrush and elements associated with the connecting members for sensing a load on the spring.

3. An article of claim 2, wherein the spring forms part of a head portion of a power toothbrush and wherein the spring includes a memory means for identifying said head portion and electrically conducting means connecting said memory means to a handle portion of the toothbrush.

4. An article of claim 1, wherein the first member and the second member are substantially parallel and remain substantially parallel during rotation of the spring.

5. An article of claim 1, wherein the first member and the second member are nonparallel, such that the second member has both rotational and translational motion in response to movement of the driving member.

6. An article of claim of claim 1, wherein the leg members include three equally spaced leg members.

7. An article of claim 1, wherein the movement of the driving member is rotational.

8. An article of claim 1, wherein the leg members are straight and tubular.

9. An article of claim 1, wherein the leg members are arcuate in configuration.

10. An article of claim 1, wherein the leg members bifurcate between the upper and lower members.

11. An article of claim 1, wherein the leg members change in size along their length in a preselected manner.

12. An article of claim 1, wherein the second member is smaller in diameter than the first element.

13. An article of claim 1, wherein the leg members and the first member are circular in cross-section.

14. An article of claim 1, wherein the leg members and the first member are elliptical in cross-section.

15. An article of claim 1, wherein the leg members are connected to the first member in a slot arrangement, such that the leg members move a short distance to an end of said slot, at which point the leg members begin to twist.

16. An article of claim 1, including connecting members which extend from the first member and include portions thereof which fixedly connect the first member to the appliance body.

17. An article of claim 1, wherein the spring has a tubular configuration.

18. An article of claim 1, wherein the spring has a conical configuration.

19. An article of claim 1, wherein the spring forms part of a head portion of a power toothbrush which includes a fluid line which extends through the spring.

20. A spring adapted for rotational action for use in a power toothbrush, comprising:
    a driven member which forms part of a head portion of a power toothbrush adapted to receive a driving member from a power toothbrush body member, wherein when the driving member moves through a selected range of movement, the driven member rotates in response thereto;
    a seal member positioned between the head portion of the toothbrush and the toothbrush body member; and
    at least two leg members extending from the driven member and including connecting members at the ends thereof for connecting the leg member and hence the driven member to the toothbrush body member, wherein the leg members are constructed and arranged and are characterized such that when the driving member moves to an end point of its range of movement, having rotated the driven member and the leg members attached thereto, the energy stored in the spring thereby tends to return the spring toward its original position.

21. An article of claim of claim 20, wherein the leg members include three equally spaced leg members.

22. An article of claim 20, wherein the movement of the driving member is rotational.

23. An article of claim 20, wherein the leg members are straight and tubular.

24. A spring adapted for rotational action, comprising:
    a first member substantially fixably attached to an appliance body member, the first member having an open center area extending through said first member to permit an appliance driving member which rotates in operation to extend freely therethrough, wherein the first member is an upper ring member which substantially encircles the driving member;

a second member spaced apart from the first member and adapted to receive said appliance driving member, wherein when the driving member moves through a selected range of movement, the second member rotates in response thereto, wherein the second member is a lower disc member having a central opening through which the driving member is tightly fitted in such a manner that as the driving member rotates, the second member rotates therewith relative to the fixed first member; and at least two leg members connecting the first and second members, wherein the leg members are constructed and arranged and characterized such that when the driving member moves to end points of its range of rotational movement, having rotated the second member with the leg members attached thereto, the energy stored in the spring thereby tends to return the spring toward its original center position.

* * * * *